(12) United States Patent  
Siller

(10) Patent No.: US 8,733,345 B2  
(45) Date of Patent: May 27, 2014

(54) INHALATION DEVICE AND HEATING UNIT THEREFOR

(76) Inventor: Friedrich Siller, Goeppingen (DE)

( * ) Notice: Subject to any disclaimer, the term of this patent is extended or adjusted under 35 U.S.C. 154(b) by 879 days.

(21) Appl. No.: 12/442,524

(22) PCT Filed: Oct. 4, 2007

(86) PCT No.: PCT/EP2007/008603  
§ 371 (c)(1),  
(2), (4) Date: Mar. 23, 2009

(87) PCT Pub. No.: WO2008/043474  
PCT Pub. Date: Apr. 17, 2008

(65) Prior Publication Data  
US 2010/0083959 A1  Apr. 8, 2010

(30) Foreign Application Priority Data

Oct. 6, 2006  (DE) .......................... 10 2006 048 325  
Jun. 6, 2007  (DE) .......................... 10 2007 026 979

(51) Int. Cl.  
*A61M 15/06* (2006.01)  
*A24F 47/00* (2006.01)

(52) U.S. Cl.  
CPC .............. *A61M 15/06* (2013.01); *A24F 47/006* (2013.01)  
USPC .................................................. 128/202.21

(58) Field of Classification Search  
CPC ... A24F 47/002; A24F 47/004; A24F 47/006; A61M 11/041; A61M 11/048; A61M 15/06  
USPC ........ 128/202.21, 200.24; 131/330, 335, 361, 131/194, 195, 198.1, 270–273  
See application file for complete search history.

(56) References Cited

U.S. PATENT DOCUMENTS 4,036,224 A   7/1977  Choporis et al.  
4,969,476 A  11/1990  Bale et al.  
(Continued)

FOREIGN PATENT DOCUMENTS

DE    2704218 A1   8/1978  
DE   19854008 A1   5/2000  
(Continued)

OTHER PUBLICATIONS

Dr. Dirk Kehrwald, Dr. Stefan Rief, Fraunhofer Institute for Industrial Mathematics ITWM: Simulation of air flow velocities in cylinders and theoretical questions on permeability, Expert Report, Apr. 25, 2008, p. 1-8, Kaiserslautern, Germany.

(Continued)

*Primary Examiner* — Lynne Anderson  
*Assistant Examiner* — Bradley Philips  
(74) *Attorney, Agent, or Firm* — Smartpat PLC; Axel Nix

(57) ABSTRACT

The invention relates to a heating unit for an inhalation device for the inhalation administration of an inhalation mixture of air and at least one additive material, having a fuel storage (252) which is filled or can be filled with a thermally combustible solid or liquid fuel (258), and with a combustion chamber (256) for the combustion of the fuel (258), which is essentially sealed from the surroundings by a combustion chamber wall (222). The invention further relates to an inhalation device (210) with such a heating unit.

Figure 2A:
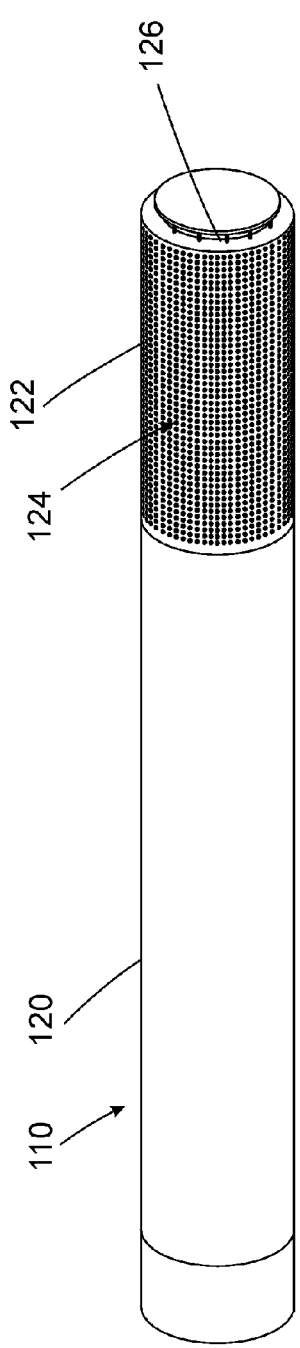

According to the invention, the combustion chamber (256) is designed for forming a flame, and the combustion chamber wall (222) has at least some micro openings (224). The micro openings are designed in such a way that the sum of the outer side lengths of all micro openings (224) is at least 140 mm, and the sum of the outer side lengths of the micro openings (224) per surface in the area of the combustion chamber wall (222) averages at least 80 mm/cm$^2$.

Application as cigarette substitute or as aid for nicotine withdrawal.

23 Claims, 5 Drawing Sheets

(56) References Cited

U.S. PATENT DOCUMENTS

| | | | |
|---|---|---|---|
| 5,099,861 A | | 3/1992 | Clearman et al. |
| 5,144,962 A | * | 9/1992 | Counts et al. ................ 131/194 |
| 5,188,130 A | * | 2/1993 | Hajaligol et al. ............. 131/359 |
| 5,345,951 A | * | 9/1994 | Serrano et al. ................ 131/194 |
| 5,402,803 A | * | 4/1995 | Takagi .......................... 131/200 |
| 5,750,964 A | * | 5/1998 | Counts et al. ................ 219/535 |
| 5,944,025 A | | 8/1999 | Cook et al. |
| 6,164,287 A | | 12/2000 | White |
| 6,532,965 B1 | * | 3/2003 | Abhulimen et al. .......... 131/194 |
| 6,536,442 B2 | * | 3/2003 | St. Charles et al. ........... 131/194 |
| 6,598,607 B2 | * | 7/2003 | Adiga et al. ................... 131/194 |
| 6,823,873 B2 | * | 11/2004 | Nichols et al. ................ 131/365 |
| 7,488,171 B2 | * | 2/2009 | St. Charles et al. ........... 431/329 |
| 7,997,280 B2 | * | 8/2011 | Rosenthal ..................... 131/191 |
| 2003/0091458 A1 | * | 5/2003 | Weber et al. ..................... 420/8 |
| 2004/0031495 A1 | * | 2/2004 | Steinberg ...................... 131/194 |
| 2004/0255965 A1 | * | 12/2004 | Perfetti et al. ................. 131/353 |
| 2006/0065228 A1 | * | 3/2006 | Pelrine et al. ............... 123/193.2 |
| 2008/0087290 A1 | * | 4/2008 | Taniguchi et al. ............ 131/332 |

FOREIGN PATENT DOCUMENTS

| | | |
|---|---|---|
| DE | 19854009 A1 | 5/2000 |
| EP | 0472367 A1 | 2/1992 |
| EP | 0949873 A1 | 7/1998 |
| EP | 1059854 A1 | 9/1999 |
| EP | 1439765 A1 | 5/2003 |
| EP | 1441607 A1 | 5/2003 |
| JP | 2000 236 856 A | 9/2000 |
| WO | WO 2006/082571 A | 8/2006 |

OTHER PUBLICATIONS

Dr. Ing. W. Wuerz, Dr. Igor Braga, Institute of Aerodynamics and Gasdynamics, University of Stuttgart: Measurement of air flow velocities in cylinders, Expert Report, Apr. 21, 2008, p. 1-5, Stuttgart, Germany.

* cited by examiner

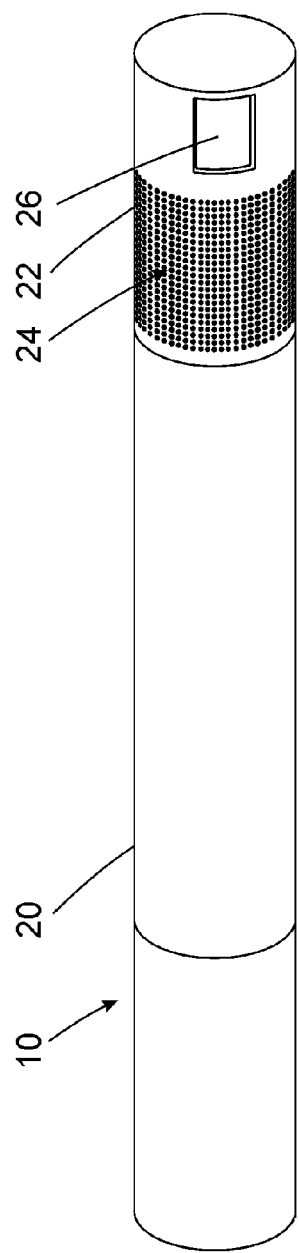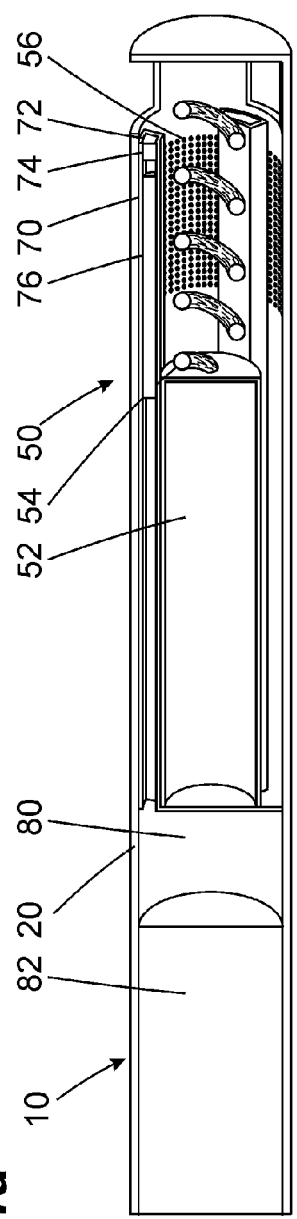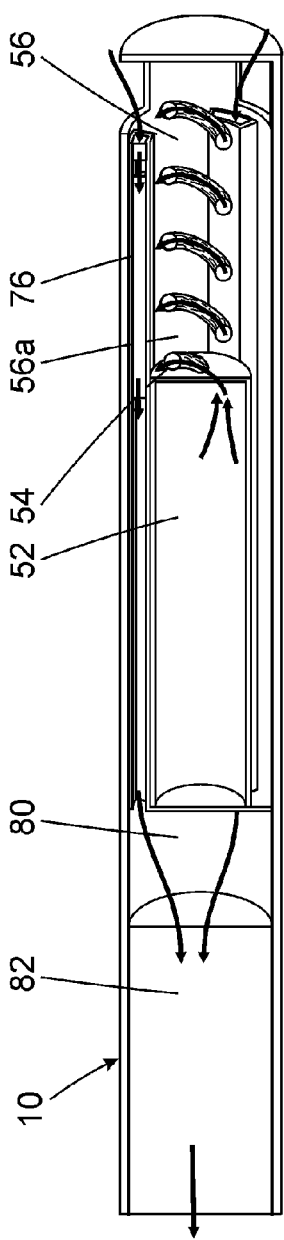

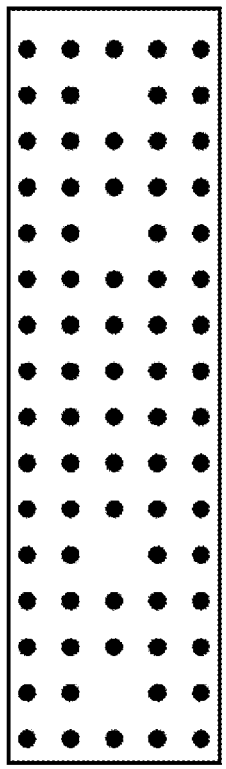 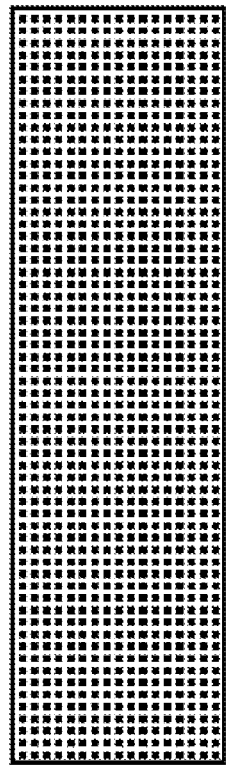 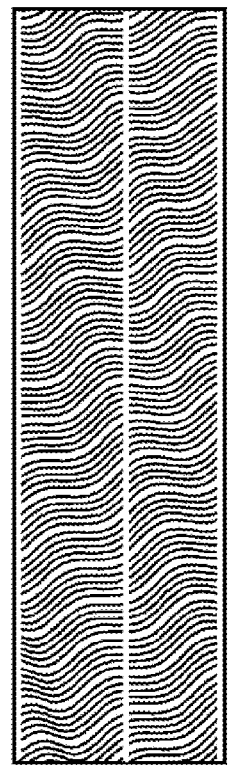
*Fig. 5a*  *Fig. 5b*  *Fig. 5c*

INHALATION DEVICE AND HEATING UNIT THEREFOR

TECHNICAL FIELD

The invention relates to a heating unit for an inhalation device for the inhalation administration of an inhalation mixture of air and at least one additive material, having a fuel storage which is filled or can be filled with a thermally combustible solid or liquid fuel, and with a combustion chamber for the combustion of the fuel, which is essentially sealed from the surroundings by a combustion chamber wall. The invention further relates to an inhalation device for the inhalation administration of an inhalation mixture of air and at least one additive material with a mouthpiece, an inhalation mixture generator with an air inlet opening, and a heating unit for the combustion of a fuel and for heating the air and/or the additive material and/or the inhalation mixture, the inhalation mixture generator being directly connected to the mouthpiece or via an inhalation duct.

BACKGROUND OF THE INVENTION

Generic inhalation devices are known in the prior art. The inhalation devices in particular serve to substitute normal tobacco consumption in the form of cigarettes or other tobacco products. In addition they can be used in particular for the withdrawal in the case of smokers. Here generic heating units serve to warm up the air or the additive materials. U.S. Pat. No. 5,099,861 A, U.S. Pat. No. 4,969,476 A, and EP 0472367 A1 disclose inhalation devices where the thermal energy is provided by a glowing coal element without a flame, the combustion gases that are produced being also inhaled by the user. DE 2704218 A1 discloses an application where a heating element is heated by the flame of a heating source, for example a lighter. U.S. Pat. No. 6,164,287 A and JP 2000 236 865 A disclose inhalation devices that combust a gaseous fuel. DE 19854009 A1 discloses an inhalation device where a heating means, in particular propane gas, is combusted in a closed combustion chamber. U.S. Pat. No. 6,532,965 B1 discloses inhalation devices where ethanol is combusted in a combustion chamber. U.S. Pat. No. 6,598,607 B2 and U.S. Pat. No. 5,944,025 A disclose inhalation devices where ethanol is combusted without a flame in a catalytic reaction.

Concerning the prior art, it is considered disadvantageous that the handling of the known inhalation devices differs significantly from the conventional handling of a cigarette as known to a smoker, that the flame does not burn in the combustion chamber with sufficient stability, and/or that stabilization of the combustion process requires complicated technical measures.

OBJECT AND SOLUTION

The object of the invention is to further develop generic heating units and inhalation devices in terms of uncomplicated handling and reliable functioning.

According to the invention, this is achieved by a generic heating unit with the characterizing features of claim 1.

In the combustion chamber of the heating unit, the fuel that has been conveyed thereto or has been stored there directly is combusted with a flame. The heating unit is preferably designed such that no further supply of energy from outside is necessary to maintain the flame after it has been ignited. The heat that has been generated is used in an inhalation mixture generator assigned to the heating unit to produce an aerosol to be inhaled. Use of the heat can take place by warming the air before it enters into an inhalation mixture generator and/or by directly warming the additive materials to be inhaled.

For integrating the heating unit into an inhalation device that in terms of its size does not significantly exceed the size of a cigarette, the heating unit is preferably smaller than 11 mm in two of the three dimensions.

The combustion chamber exhibits a free spreading area for the flame with a diameter of at least 5 mm, preferably at least 7 mm. The combustion chamber is preferably of cylindrical design and has a diameter of at least 7 mm and a length of at least 7 mm.

The combustion chamber is that space where the flame can unfold as intended during use of the heating unit. The combustion chamber wall is that wall that separates the combustion chamber from an outside environment where the oxygen for the combustion originates. Walls to an adjoining inhalation mixture generator or to the fuel storage are not part of the combustion chamber wall.

The details concerning the outer side lengths of the micro openings refer to that section of the combustion chamber wall in which the micro openings are envisaged. The micro openings are preferably distributed largely homogenously across the combustion chamber wall. If the outer side length density varies across the combustion chamber wall, the details stated here concerning the outer side length density refer to a section of the combustion chamber wall in which 80% of the micro openings are located in relation to the relatively highest outer side length density.

The micro openings that can be provided in a regular, for example matrix-like, or in an irregular arrangement, guarantee a continuous supply of oxygen to the flame through the combustion chamber wall and thus enable the flame to be maintained during the entire period of use. In a particular embodiment, the micro openings can be arranged in the form of characters so that trademarks and similar can be applied without a printing process.

The small size of the openings protects the flame against outside movements of air and thus stabilizes the combustion process. In the case of wind gusts, the edges of the openings produce eddies in the combustion chamber wall that slow down the air passing through. Seen aerodynamically, the outer side length of the openings is thus decisive for the flow resistance of the combustion chamber wall. With the same open area, a higher outer side length per surface leads to an increase in the flow resistance of the combustion chamber wall. In the case of a wind gust, the air movement that could lead to the flame being extinguished is thereby reduced inside the combustion chamber. Micro openings with high outer side length densities therefore enable the flame to be stabilized in contrast to large openings.

In the context of this invention, the outer side of the micro openings is understood to be the transition area between combustion chamber wall and micro opening, the corresponding length dimensions referring to an optical resolving power with a maximum resolution of 5 micrometers. In the case of micro openings running perpendicularly to the direction of extent of the wall, the length dimensions refer to a planar projection. In the case of micro openings that do not run perpendicularly to the direction of extent of the wall, for example when using a braid, the absolute filter fineness is used to determine the outer side lengths of the openings. For determining the outer side lengths, the maximum outer side length of an object that fits through the respective micro opening is therefore decisive.

For supplying the combustion chamber with the fuel, a wick or a pressure pipe can be provided. The wick or the pressure pipe can preferably be designed with one or more of the following attributes. The wick can be designed as a glass fiber wick that carries the liquid fuel into the combustion chamber by capillary forces. The softening temperature of the wick or of its major part can be more than 800° C., preferably more than 1000° C., to enable a thin design of the wick and thus a low oxygen demand of the flame. Such a wick can for example comprise fused quartz. To avoid transition losses, the wick itself can represent the fuel storage and for this purpose exhibit a fuel storage section that is preferably folded so as to save space. Several wicks can be provided that extend into the combustion chamber with different distances, to enable the flame to be maintained even after one of the wicks has gone out, or a stronger heat generation by several flames in the case of a strong oxygen supply.

Particular embodiments contemplate the provision of at least one thin glow element in the area of the combustion chamber, which can be made to glow by the flame. The glow element visualizes an operating state of the heating unit, this being particularly convenient for fuels with an invisible flame. The glow element is preferably designed as a chromium-nickel wire.

Preferably relating to the use in a cylindrical inhalation device, the micro openings are provided on a lateral jacket wall of the combustion chamber. Preferably an area of the micro openings is provided in the jacket wall and extends in the main direction of extent of the inhalation device over a length of between 5 mm and 20 mm.

The outer side length density is the sum of the outer side lengths of the micro openings per surface. The outer side length density is determined by determining the outer side length of each individual opening, then summing over all openings and dividing by the surface over which the openings are distributed.

The micro openings are particularly advantageous with regard to the inflow behavior of the air and the protection of the flame, if the outer side length density is more than 120 $mm/cm^2$, in particular more than 200 $mm/cm^2$. The outer side length density is preferably more than 400 $mm/cm^2$, in particular more than 800 $mm/cm^2$. The total outer side length should amount to at least 140 mm and in particular be over 210 mm. The total outer side length preferably amounts to more than 350 mm, advantageously to 700 mm, in particular more than 1400 mm.

A total outer side length of 140 mm for an outer side length density of 80 $mm/cm^2$ has proven to be a particularly preferable combination. 210 mm or more total outer side length for 120 $mm/cm^2$ or a higher outer side length density, for example 350 mm for 200 $mm/cm^2$, 700 mm for 400 $mm/cm^2$, 1400 mm for 800 $mm/cm^2$, are even more advantageous. A higher outer side length density and a higher total outer side length are each regarded as advantageous. In this context, it is furthermore an advantage if opposite edges of a micro opening are spaced apart from each other by at most 1.4 mm, to prevent the flame from reaching through. The micro openings can be of different shapes. The manufacture of round and square micro openings is particularly simple. Other shapes such as elongate, line-shaped, or wiggly openings are also suitable.

In a further development of the invention, the micro openings themselves have an average opening surface of less than 1.5 $mm^2$, preferably an opening surface of less than 1 $mm^2$, in particular preferably an opening surface of less than 0.5 $mm^2$. Furthermore, they preferably have an opening surface of more than 0.0002 $mm^2$, in particular more than 0.0004 $mm^2$. Such opening surfaces are advantageous with regard to the oxygen supply and to avoid disadvantageous blasts of air right into the combustion chamber.

The open area of the combustion chamber wall that is produced by the micro openings preferably occupies between 10% and 50%, in particular between 20% and 45%, of that section of the combustion chamber wall in which the micro openings are provided.

In a further development of the invention, the combustion chamber wall is formed at least partly by a metal fabric or a metal braid. Metal fabrics and braids with a mesh value between 150 and 635, metal fabrics and braids with a mesh size between 0.02 mm and 0.08 mm, and/or metal fabrics and braids with a wire gauge of between 0.019 mm and 0.05 mm have proven to be advantageous.

As an alternative thereto, also the formation of the combustion chamber wall as a metal foil with micro openings made therein can be advantageous. The micro openings can be made therein for example mechanically or by means of an etching method.

Embodiments are particularly preferred, where the wall material is thin and/or has a relatively low heat capacity. The result is that heat introduced during the course of the ignition is not carried away to heat the wall but almost exclusively serves to ignite the flame. The result is an easier ignitability of the flame in the combustion chamber. When using a metal fabric or a metal foil as wall material, for example from chromium-nickel steel, the weight per unit area should be below 300 $grams/m^2$.

In a further development of the invention, the combustion chamber is accessible from the outside only in the area of at least and preferably one ignition access. The accessibility is to be understood here such that on igniting the heating unit an ignition flame can gain access only through the ignition access. A contiguous surface area of at least 2 $mm^2$ is regarded as the ignition access, of which at least 90% is free and forms an open duct between the surroundings and the combustion chamber. The ignition access is preferably designed as a longitudinal slot with a width of at least 1 mm. In a preferred variant the ignition access is provided in a lateral wall of the combustion chamber. Alternatively, the ignition access can also be arranged at the distal end of the heating unit relative to its state in which it is connected to an inhalation device. The ignition access is preferably designed by surface sections that are arranged one behind the other and/or offset relative to each other so that the air is diverted at least once on entering the combustion chamber.

In particular an ethanol/water mixture is suitable as fuel, since ethanol enables an almost complete combustion, can be inflamed easily, and is nontoxic. Other fuels can however also be used, use of toxic fuels also being possible if the air that is drawn in, is drawn in separated locally from the combustion chamber. Apart from ethanol, other alcohols, aldehydes, ketones, esters, n-alkanes with one to four carbon atoms, n-alkanes with five to twenty carbon atoms, branched or cyclic alkanes with four to twenty carbon atoms have proven to be convenient.

In a further development of the invention, a liquid fuel having a viscosity of at least 10,000 mPa·s is used. The flame in the combustion chamber heats the surface of this fuel gel above the boiling point of the fuel. The fuel is evaporated at the surface of the fuel gel as a result and supplied continuously for maintaining the flame. The fuel gel permits simple handling and in addition allows an arrangement directly in the combustion chamber and thereby to dispense with wicks. For low-viscosity fuels the desired viscosity can be achieved by adding viscosity-increasing additives like polyacrylic acid or cellulose.

In a further development of the invention, the fuel storage is closed by means of a gastight closure that can be removed by supplying heat. This prevents the fuel from volatizing already before igniting. The closure is removed by supplying heat during the course of the ignition of the flame of the inhalation device. For example treated paper, wax, tin foil, or plastic foil are contemplated as materials for the closure.

As an alternative thereto, it can be provided that the fuel storage is closed by means of a gastight closure that can be removed or ripped open by a pressure that can be applied manually on the fuel storage, preferably by two-sided pressure on the heating unit in the area of the fuel storage. Such a gastight closure can in particular be a foil that is provided at an outlet of a fuel tank that otherwise exhibits a stable shape. In the case of a shape according to this further development, the user can transfer the heating unit into a usable state by exerting a slight pressure.

It is particularly advantageous if an outside wall of the fuel storage can be strongly deformed elastically and is closed off by a closure foil that can be deformed elastically to a lesser extent. A joined deformation of the wall and of the closure foil results in the closure foil tearing open on reaching the tearing limit. On discontinuation of the deformation force the fuel storage returns to its original shape and then permits the fuel to escape through the torn closure foil.

In a further development of the invention, the fuel storage can be connected releasably to the heating unit, and/or can be refilled. This permits the fuel storage to be refilled or to be designed so as to be exchangeable, whereby other components of the heating unit, in particular the combustion chamber, can be used more than once.

The invention, furthermore, relates to a generic inhalation device where the heating unit is designed according to the type described above.

The user can draw in air through the mouthpiece that can for example be designed as a hollow pipe or as a filter, the air then being guided through the inhalation mixture generator and being mixed there with at least one additive material. The mixture is then inhaled by the user.

Mixing of the air with the additive materials is achieved by the high temperature of the air heated in the combustion chamber and/or of the heated additive materials. As a result, an inhalable aerosol is formed from the drawn-in air and the additive materials. The heat also achieves the separation of the additive materials from a carrier structure, in which the additive materials are stored. The heat can, furthermore, effect a chemical modification of the additive materials and/or of the carrier structure.

The heat generated in the combustion chamber is supplied preferably directly to the inhalation mixture generator and/or to the drawn-in air, it being possible for the flame in the combustion chamber to heat the inhalation mixture generator and/or the air directly, or indirectly via heat-conducting materials. To prevent the flame in the combustion chamber to be drawn in together with the air right into the inhalation mixture generator, a flame barrier, for example made from a metal foil, can be provided upstream of the inhalation mixture generator.

Before mixing with the air that flows through, the additive materials are preferably already stored in an additive material storage inside the inhalation mixture generator. Alternatively, they can be stored in a spatially separate additive material storage. The additive materials are preferably stored in a porous carrier material; activated carbon, aluminum oxide, calcium carbonate, diatomaceous earth, cellulose, or tobacco material being particularly suitable therefor. It may also be convenient to store the additive materials in plant parts, in particular in those plant parts that produce the additive materials naturally. This is convenient in particular in the case of tobacco with nicotine or in the case of medicinal herbs with active substances. The additive material storage can be formed by a cigarette or by a tobacco unit that is at least partly encased or otherwise joined together. For inhalation mixture generators with several additive materials, they are preferably arranged one behind the other, more heat-sensitive additive materials being arranged in a rear area of the flow path of the air.

The combustion chamber is preferably of a design and arranged in the inhalation device such that the flame is visible from outside. It is preferably accessible such that lighting the flame is possible from outside using the means that are common in the case of cigarettes, such as matches or lighters.

The components of the inhalation device are preferably arranged in a homogenous housing with a common outside wall. This is particularly advantageous if the shape of the housing approximates conventional tobacco products such as a cigarette. Embodiments are preferred where the outside wall consists at least partly of a material that is not or hardly flammable, for example pretreated paper, metal, ceramic, or porcelain.

The main application of inhalation devices according to the invention, is to substitute conventional tobacco products where the active ingredients and additive materials are released by combusting tobacco. In an inhalation device according to the invention, the additive materials can be chosen very selectively while avoiding additive materials and combustion products that cause diseases, in particular carcinogenic ones. It is in particular additive material combinations with the active ingredients nicotine and aroma substances that lend themselves for a cigarette substitute. In particular oils, tobacco plant extracts, and natural and nature identical aroma substances are convenient as flavor forming additive materials. Furthermore, preferably also tasteless, fog producing substances such as polyols, in particular propylene-glycol or glycerol, are convenient to imitate conventional cigarettes. Conventional tobacco can also be used, whose harmfulness can be lowered drastically by avoiding a combustion of the tobacco.

In addition to the use as a replacement for conventional tobacco products, other uses are also possible, for example medicinal applications where the additive material possesses in particular a pharmaceutical effect. This comprises for example pain killers and tranquilizers.

In a further development of the invention, the inhalation device exhibits an outside wall to the surroundings that disintegrates under the influence of heat or consists of a material or a combination material that becomes fragile under the influence of heat. At the same time the combustion chamber is preferably being displaced during the course of usage, while the outside wall disintegrates gradually in accompanying this process. The disintegration at the same time takes place preferably without thermal combustion. In terms of handling, the disintegration of the outside wall is similar to the combustion process of a normal cigarette. As in the case of a cigarette, the user can knock off the ash from the inhalation device step by step.

The outside wall can, for example, consist of treated paper that is coated with a nonflammable substance, as for example sodium silicate on one or both sides. The treatment of the paper slows the oxidation during heating. The outside wall thereby slowly loses its rigidity and can be removed or drops off after a certain time. Another possibility envisages that the material of the outside wall contains constituents of aluminum trihydrate, carboxymethyl cellulose, sodium borate, wood pulp, and glycerin. Materials of this type are described in DE 4336160 A1 and U.S. Pat. No. 4,019,520 A1 whose content is incorporated into this description by explicit reference. The outside wall can also have a core of a thermoplastic material and a sheath from a nonflammable substance. Such a construction feels like a cigarette, and the ash can be knocked off after thermal softening of the core. In the ideal case, the thermoplastic material is a plastic, for example a nonwoven from polyethylene. The sheath can consist of sodium silicate or calcium sulfate hemihydrate. The outside wall can also consist of a material that exhibits a constituent of an inorganic salt, the inorganic salt losing water and/or carbon dioxide under the influence of heat. Suitable materials can be gathered from U.S. Pat. No. 3,356,094, in particular column 4, lines 46ff. In particular magnesium sulfate heptahydrate, magnesium carbonate trihydrate, other magnesium carbonates, potassium bicarbonate, or calcium sulfate offer themselves as salts. To selectively influence the disintegration of the outside wall, predetermined weak grooves can be provided in the wall.

In a further development, the outside wall consists of heat-resistant wall segments, for example of metal, ceramic, or porcelain, that are joined using a preferably nontoxic joining means, for example polyethylene. It is also possible to use a paper-like cover that connects the wall segments and that is treated such that it smolders away only slowly and at the same time releases the wall segments bit by bit.

In a further development, the heating unit is designed as a device that can be handled separately and that can be connected releasably to the inhalation mixture generator. This permits reuse of the heating unit, while the inhalation mixture generator, preferably jointly with the mouthpiece and an additive material storage, is handled as a disposable component. The components mouthpiece, inhalation mixture generator, and additive material storage, can in particular also be formed jointly by a commercially available cigarette or a prepacked tobacco unit with a mouthpiece, on which the heating unit can be mounted such that the air that has been drawn in through the cigarette or the tobacco unit is heated by means of the flame in the combustion chamber of the heating unit. Such a heating unit is preferably attached at the cigarette or the tobacco unit at the distal end, which is the end facing away from the user.

The purpose of this combination, composed of the heating unit and such a tobacco product, is to provide the tobacco product with heat from the heating unit, so as to achieve a separation of the active ingredients and/or flavors from the tobacco. The heat produced in the combustion chamber is supplied to the tobacco via convection and/or heat conduction and heats it to 150° C. up to 400° C. As a result, the additive materials are released by the tobacco without the tobacco product igniting. The user can continue using his accustomed tobacco product, its harmful properties being reduced in the process.

In the case of such a heating unit that is suitable for use with a normal cigarette, the attachment would preferably have to be designed such that it completely or largely encloses the section of the cigarette that is filled with tobacco. It is also possible to imagine embodiments where even the mouthpiece is part of the attachment, so that only the tobacco of the cigarette is used. In a further development of the invention, the heating unit can also be placed on the air inlet opening of a pipe.

In a further development of the inhalation device, an additive material storage is provided that is designed to be separate from the inhalation mixture generator, the additive material storage being designed such that it can be replaced and/or refilled. The replaceability of the additive material storage permits to use certain components several times, such as for example the housing, the heating unit and/or the mouthpiece. The additive material storage can be put onto the inhalation device in a simple manner or inserted into the inhalation device.

In a further development of the invention, the inhalation device exhibits an essentially elongate structure, preferably a cylindrical structure, the mouthpiece being arranged at a proximal end of the inhalation device and the heating unit being arranged in the area of the distal end of the inhalation device. In terms of the shape, such an inhalation device comes particularly close to a cigarette or a cigar and thus forms a good cigarette substitute.

In a further development of the invention, the inhalation device exhibits a polyol storage that is arranged such that the polyol contained can be heated by the heating unit and can be transformed into an aerosol. This aerosol is then perceived as a visible smoke similar to the smoke of a cigarette. It can additionally be provided with aromas. The polyol can initially be stored in a closed storage. A design where the polyol is provided as a coating on parts of the inhalation device, in particular on the combustion chamber wall, and can be converted there into an aerosol by heating the heating unit, is simpler.

SHORT DESCRIPTION OF THE DRAWINGS

Figure 2B:
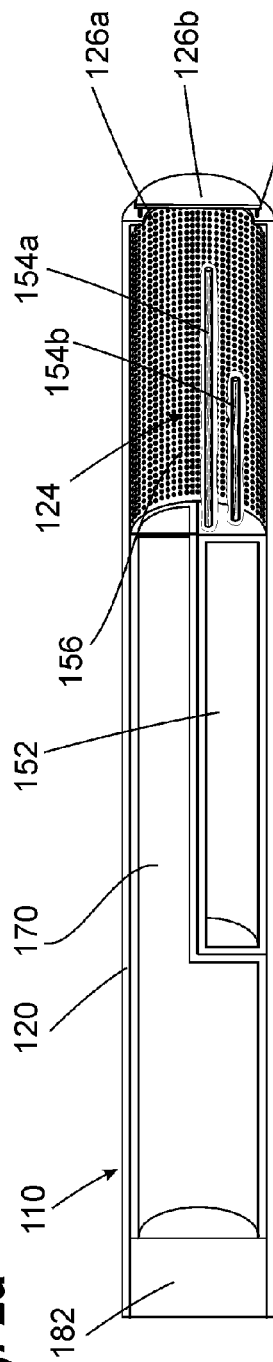
Figure 2C:
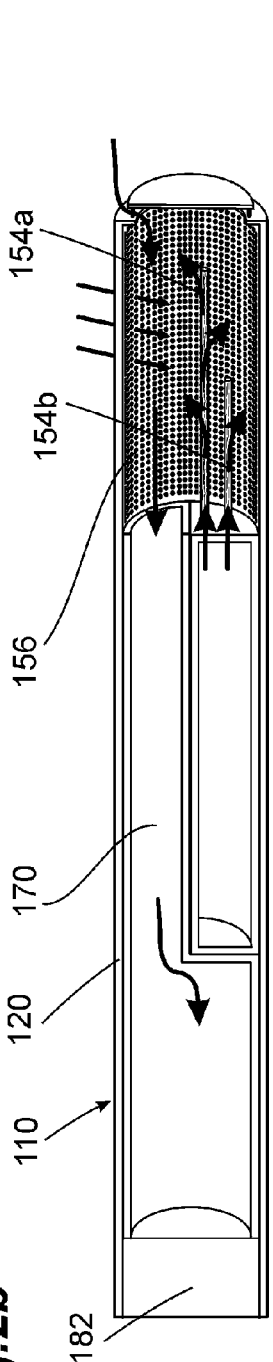
Figure 3A:
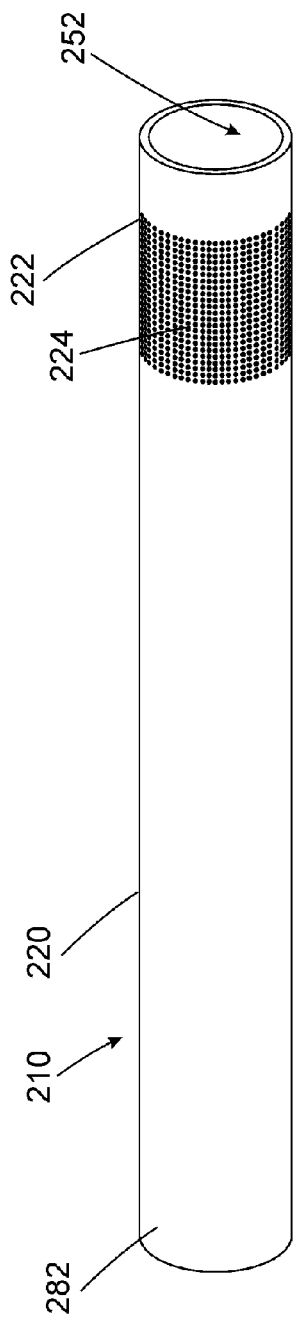
Figure 3B:
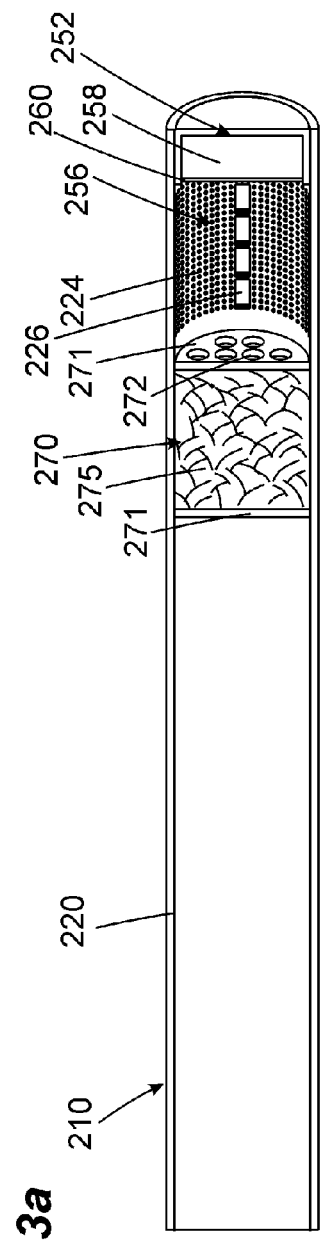
Figure 3C:
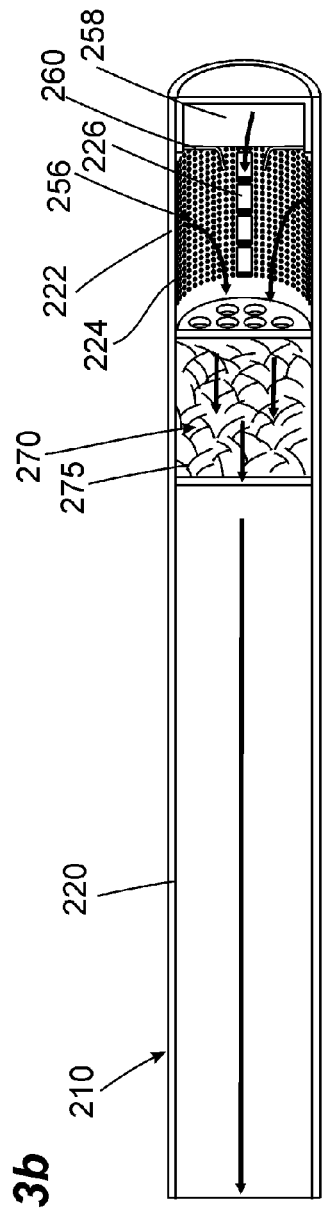
Figure 4A:
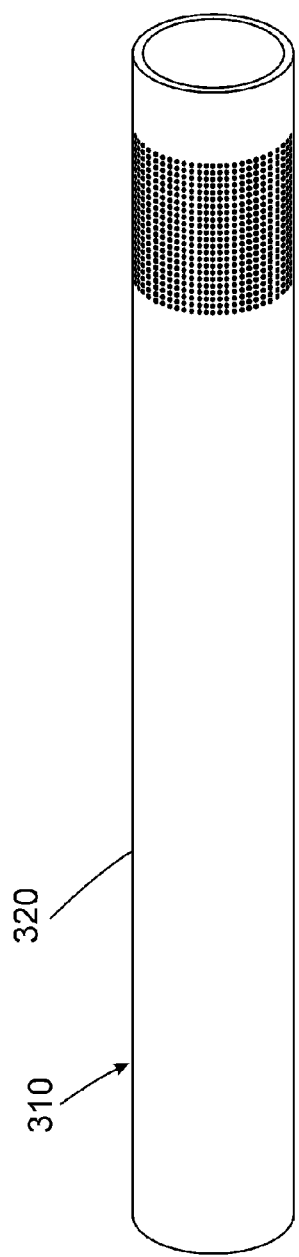
Figure 4B:
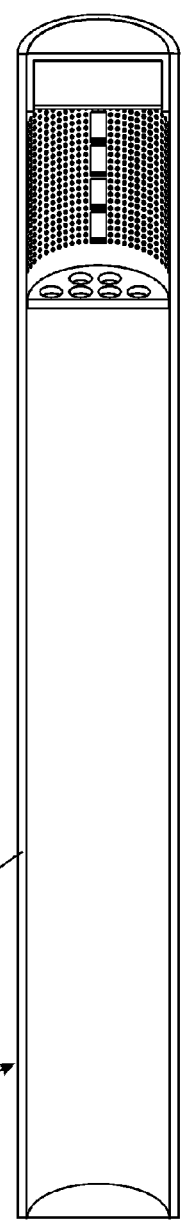
Figure 4C:
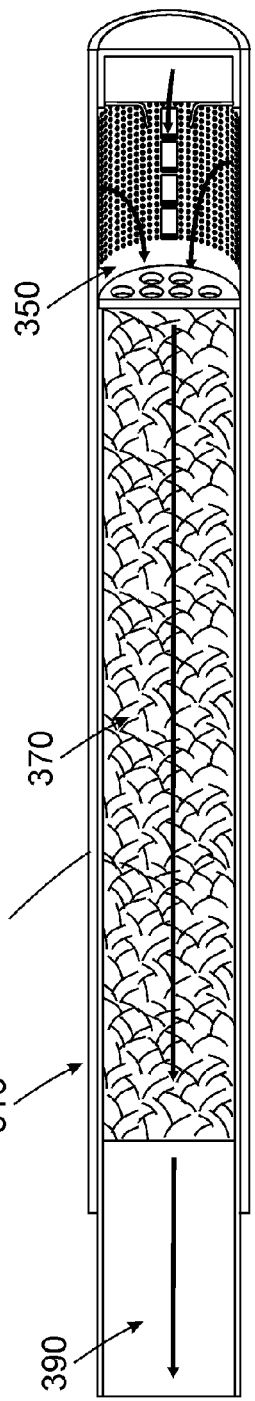

Further advantages and features of the invention become apparent from the claims and the following description of preferred exemplary embodiments of the invention that are illustrated with the aid of the drawings. The exemplary embodiments only serve as an explanation and do not limit the invention. In the drawings:

FIGS. 1a to 1c show a first embodiment of an inventive inhalation device in an uncut and a cut view and in an operating state, FIGS. 2a to 2c show a second embodiment of an inventive inhalation device in an uncut and a cut view and in an operating state, FIGS. 3a to 3c show a third embodiment of an inventive inhalation device in an uncut and a cut view and in an operating state, FIGS. 4a to 4c show a fourth embodiment of an inventive inhalation device in an uncut and a cut view and in an operating state, and FIGS. 5a to 5c show different combustion chamber walls in the unwound state.

DETAILED DESCRIPTION OF THE EXEMPLARY EMBODIMENTS

In the context of the invention, the proximal end is always meant to be the end of a component facing the user, and the distal end is meant to be that facing away from the user. Components of the different exemplary embodiments that are comparable in terms of their function have the same last two digits of the reference symbol.

FIGS. 1a to 1c show a first embodiment of an inventive inhalation device 10. It is of cylindrical design and has an outside wall 20 that is provided with micro openings 24 at a distal end of the inhalation device 10 as combustion chamber wall 22. The wall 20 has a recess 26 at the distal end face.

FIG. 1b shows the inside construction of the inhalation device 10. A heating unit 50 is provided at the distal end of the inhalation device 10. The heating unit has a fuel storage 52 in which the fuel is stored in a liquid state. A wick 54 extends from the fuel storage 52 into a combustion chamber 56 that is provided at the distal end of the inhalation device and that is surrounded by the combustion chamber wall 22. The wick 54 is formed like a screw. A total of three inhalation mixture generators 70 are arranged on an inside of the outside wall 20 distributed over the circumference and each extends essentially axially starting from the distal end of the inhalation device in the direction of the proximal end. The inhalation mixture generators 70 are designed as hollow ducts into whose air inlet apertures 72 glass fiber plugs 74 that act as a flame barrier are inserted. Additive materials 76 are stored in the tubular inhalation mixture generators 70 in a porous carrier substance. At a proximal end of the inhalation mixture generators 70 a homogenization chamber 80 is connected into which all three inhalation mixture generators 70 open. The proximal end of the inhalation device 10 is formed by a mouthpiece 82 with an inserted filter that completely fills the cross section of the outside wall 20.

FIG. 1c clarifies the method of operation of the inhalation device 10. The inhalation device is put into the mouth with its proximal end like a cigarette. It is then lighted by holding an external flame, for example from a lighter or from a match, to the distal end of the inhalation device 10. This lights the wick 54 that is supplied with a fuel from the fuel storage 52, for example with an alcohol. This creates a flame in the combustion chamber 56. The user can draw air into the inhalation mixture generators 70 through the mouthpiece 82. The drawn in air flows through the additive materials 76 that are stored in the porous carrier material. As a result of the heating, the additive materials 76 are given off to the air that flows in and mix with it to form an inhalation mixture. This inhalation mixture is drawn in through the homogenization chamber 80 and the mouthpiece 82.

A high degree of stability of the flame is achieved as a result of the micro openings 24 in the outside wall 20 in the area of the combustion chamber 56. In the absence of any adverse effect, as for example by wind, the flame is formed as a laminar flame in the area of the end face of the inhalation device. In case a strong air current occurs at the distal end, for example by wind or by a rapid movement of the inhalation device 10, this may result in a disruption of the laminar flame. In such a case the flame can pull back into a rear area 56a of the combustion chamber 56 that is more protected against wind, while the air supply is still being ensured via the micro openings 24.

Compared to a normal cigarette, the inhalation device 10 that has been illustrated and described exhibits considerable advantages in view of the impact on the health of the user. While a multiplicity of unwanted additive materials are also inhaled in the case of a normal cigarette that are released in particular by the combustion of the tobacco, in the case of the inhalation device 10 that has been illustrated only the additive materials 76 that are in particular free from carcinogenic combustion products are inhaled. According to the choice of the additive materials 76, a similar flavor and a similar effect with regard to the nicotine contained in cigarettes can still be achieved.

Compared to smoking a cigarette, use of the inhalation device does not represent any considerable changes. Like a cigarette, the inhalation device is lighted at its distal end and then remains in the lighted state until the additive materials 76 have been used up or the flame is made to extinguish. It can, however, also be convenient to limit the amount of fuel in the fuel storage 52 such that the fuel is used up approximately simultaneously with the additive materials 76.

FIGS. 2a to 2c show a second embodiment of an inventive inhalation device. In many regards this inhalation device 110 is similar to the embodiment of FIG. 1. If nothing else is specified below, its method of operation is the same.

The inhalation device 110 exhibits an outside wall 120 whose front end is designed as combustion chamber wall 122. A fuel storage 152, a combustion chamber 156, and an inhalation mixture generator 170 are provided inside this outside wall 120.

The arrangement of the inhalation mixture generator 170 and of the fuel storage 152 deviates from the embodiments of FIG. 1. While the inhalation mixture generator 170 occupies the entire cross section in the rear area of the inhalation device 110, the cross section splits into two semi-circular cross sectional areas in the central area of the inhalation mixture generator 170, the one being occupied by the fuel storage 152 and the other by the inhalation mixture generator 170. This simplified design is advantageous with regard to the manufacturing costs. In the embodiment shown, the inhalation mixture generator 170 has an outside wall. Depending on the design of the outside wall 120 of the inhalation device 110, such an additional wall can however be dispensed with. In this embodiment, the inhalation mixture generator 170 is of a relatively large size and can accommodate larger amounts of flavors, tobacco, or similar materials as a result.

There are considerable differences with regard to the combustion chamber 156. In the embodiment of FIGS. 2a to 2c, it is largely surrounded by the section 122 of the outside wall 120, which is provided with a plurality of micro openings 124. At the distal end of the inhalation device 110 the outside wall 120 has an access aperture 126. It is formed by an opening 126a that is covered by a wind-protection surface 126b such that ingress of air is only possible by a circumferential gap 126c that lies in between. Therefor the combustion chamber 156 is only indirectly accessible through the access aperture 126 from outside. This design permits the flame to be lighted in the combustion chamber by means of matches or a lighter, while the user has a pull at the inhalation device 110. As a result of the gap 126c that is only narrow and the fact that the air flowing in must of necessity be diverted to get from outside right into the area of the flame, it is ensured that the flame in the combustion chamber cannot be made to extinguish by a gust of wind.

Inside the combustion chamber 156, several wicks 154a, 154b of quartz glass are provided, of which only a long interior wick 154a and a short outer wick 154b are illustrated. The wicks in each case consist of fused quartz filaments with a diameter of 12.5 micrometers, about 100 to 200 filaments being processed in each wick. Fibers having a diameter of for example 50 to 100 micrometers are also well suited for use. In the nonlighted state of FIG. 2b, the wicks are surrounded by a protective foil that prevents the fuel from escaping from the combustion chamber. In an embodiment that has not been illustrated the wicks are dispensed with. Instead, the fuel is present in a gel-like state.

The inhalation device is lighted by a lighter or a match that is held close to the inhalation device 110 in the area of the gap 126c of the access aperture 126. By drawing in air, the flame of the lighter or of the match is drawn right into the area of the longer wick 154a, where it leads to the longer wick 154a being lighted. By using fused quartz as material of the wick, particularly fine wicks 154a, 154b can be used, due to the high melting point. This leads to smaller flames with a low oxygen demand.

During operation, the flame mostly burns at the front end of the longer wick 154a, since there the oxygen supply is best ensured. However, as soon as the user pulls strongly on the mouthpiece 182, air is drawn into the combustion chamber 156 through the micro openings 124 to an increased extent. This leads to a spreading of the flame at the wick 154a in the direction toward the proximal end of the wick 154a. This leads to the short wick 154b being lighted and possibly also further wicks that are arranged in a similar manner. This leads to an increase in the heat output to the air so that the necessary heat can be supplied by the flames in the combustion chamber even in the case of strong inhalation by a user.

A third embodiment can be gathered from FIGS. 3a to 3c. The inhalation device 210 that has been illustrated has a cylindrical shape with a jacket shaped outside wall 220. It is closed at the distal end by a cup shaped fuel storage 252 of chromium-nickel spring steel, the fuel storage 252 containing a fuel 258 of a gel-like consistency and being open in the direction of a combustion chamber 256. Before starting the inhalation device 210, the open side of the fuel storage 252 is closed, as can be seen in FIG. 3b, by a membrane 260 made from a material of low elasticity, for example an aluminum foil.

The combustion chamber 256 is surrounded by micro openings 224 in a combustion chamber wall section 222 of the outside wall 220. An ignition access 226 is additionally provided on one side and comprises a total of four elongate apertures between which only narrow webs are provided. An inhalation mixture generator 270 adjoins the combustion chamber 256 on the proximal side and is formed as a chamber that is filled with a mixture 275 of tobacco and tobacco extract and is closed on the combustion chamber side and on the user side by walls 271 with entrance apertures 272 or exit apertures that are not illustrated.

When using the inhalation device 210, initially the fuel storage 252 is slightly compressed from outside. As a result, it is deformed elastically, while the membrane 260 tears due to its low elasticity. Thereby the fuel 258 becomes accessible on the combustion chamber side, as illustrated in FIG. 3c. The gel-like fuel 258 is then ignited by means of a flame that is held against the access aperture 226 from outside, so that a flame forms in the combustion chamber 256 and is fed by the fuel 258. Since the combustion chamber 256 is sealed off, this flame is very stable. It is supplied continuously and reliably with oxygen through the micro openings 224, without a sudden gust of wind or something similar being able to extinguish it.

The user who pulls at the mouthpiece 282 thereby draws the air that has been heated to temperatures of more than 250° C., from the combustion chamber 256 into the inhalation mixture generator 270. There, the hot air flows through the mixture 275 and thereby dissolves the additive materials that are subsequently inhaled by the user. The time of the smoking process is limited by the amount of fuel 258 and by the amount of additive materials in the mixture 275.

The embodiment of FIGS. 4a to 4c largely corresponds to the embodiment of FIGS. 3a to 3c. The only difference is the inhalation mixture generator 370. In the embodiment of FIGS. 4a to 4c, it is formed by a commercially available cigarette 390 that is pushed into an outside sleeve 320 of the inhalation device 310. In the case of this embodiment, the core of the inhalation device consists only of the heating unit 350.

FIGS. 5a to 5c show different combustion chamber walls in the unwound state. These combustion chamber walls can be used as separate components in the case of the previously described and other inhalation devices or can be part of larger outside walls, which form a combustion chamber wall only in some sections. The wall sections that have been illustrated are strips that each are 7 mm wide and 25 mm long. They result in a cylindrical combustion chamber with a length of 7 mm and a diameter of approximately 8 mm in the finished state. The entire surface of the combustion chamber wall is 1.75 cm².

In the embodiment of FIG. 5a, a total of 75 round micro openings are provided on this surface that each have an outer side length of approximately 2 mm. The total outer side length is therefore approximately 140 mm. In relation to the surface, the outer side length is approximately 80 mm/cm². These micro opening values are regarded as minimum values in terms of the outer side lengths.

The embodiment of FIG. 5b has a total of 1093 openings that each have an outer side length of 1 mm. The total outer side length is therefore approximately 1093 mm and the outer side length related to the surface is about 625 mm/cm².

The embodiment of FIG. 5c has a total of approximately 150 line shaped openings that each have an outer side length of approximately 9 mm. The total outer side length is therefore approximately 1350 mm, and the outer side length related to the surface is about 700 mm/cm².

The embodiments of FIGS. 5b and 5c are regarded as particularly advantageous.

I claim:

1. An inhalation device (10; 110; 210; 310) for the inhalation administration of an inhalation mixture of air and at least one additive material, comprising:
  a generally cylindrical outside wall (220) having a proximal end and a distal end;
  a mouthpiece (82; 182; 282) disposed at the proximal end of the generally cylindrical outside wall (220);
  a heating unit (50; 350) for heating the air and the additive material disposed at the distal end within the generally cylindrical outside wall; and
  an inhalation mixture generator (70; 170; 270; 370) disposed within the generally cylindrical outside wall between the mouthpiece and the heating unit, the inhalation mixture generator having an air inlet opening (72; 272) towards the heating unit and an air outlet opening towards the mouthpiece (82; 182; 282),
  wherein the heating unit (50; 350) comprises
    a fuel storage (52; 152; 252) spatially separated from the inhalation mixture generator, the fuel storage configured to receive a thermally combustible solid or liquid fuel (258), and
    a combustion chamber (56; 156; 256) configured to form a flame to combust the fuel,
    and wherein micro openings (24; 124; 224) are provided in the generally cylindrical outside wall around the combustion chamber to supply oxygen to the flame and to protect the flame from wind gusts, wherein the micro openings at least partially overlap the flame.

2. The inhalation device according to claim 1,
  wherein the sum of the outer side lengths of all micro openings (24; 124; 224) is at least 140 mm and
  wherein the sum of the outer side lengths of all micro openings (24; 124; 224) per surface of the outside wall around the combustion chamber (22; 122; 222) averages at least 80 mm/cm².

3. The inhalation device according to claim 1,
  wherein the sum of the outer side lengths of all micro openings (24; 124; 224) is at least 700 mm and
  wherein the sum of the outer side lengths of all micro openings (24; 124; 224) per surface of the outside wall around the combustion chamber (22; 122; 222) averages at least 400 mm/cm².

4. The inhalation device according to claim 1,
  wherein the micro openings (24; 124; 224) have an average aperture surface of less than 1.5 mm².

5. The inhalation device according to claim 1,
wherein the micro openings (24; 124; 224) permeate between 10% and 50% of outside wall surface area around the combustion chamber (22; 122; 222).

6. The inhalation device according to claim 1,
wherein the outside wall around the combustion chamber is formed at least partly by a metal fabric or metal braid of metal wires.

7. The inhalation device according to claim 1,
wherein the outside wall around the combustion chamber (22; 122; 222) is formed at least partly by a metal foil with incorporated micro openings (24; 124; 224).

8. The inhalation device according to claim 1,
wherein the combustion chamber (56; 156; 256) is accessible from outside only in the area of an ignition access (26; 126; 236).

9. The inhalation device according to claim 1,
wherein the fuel (258) consists at least partly of one or more of the substances selected from the group consisting of alcohols, aldehydes, ketones, and esters.

10. The inhalation device according to claim 1,
wherein the fuel (258) is present in the form of a gel with a viscosity of at least 10,000 mPa·s.

11. The inhalation device according to claim 1,
wherein the fuel storage (152) is closed by means of a gastight closure that can be removed by heating.

12. The inhalation device according to claim 1,
wherein the fuel storage (252) is closed by means of a gastight closure (260) that can be removed or torn open by a pressure that can be applied to the fuel storage manually, preferably by pressure on the inhalation device from both sides in the area of the fuel storage.

13. The inhalation device according to claim 1,
wherein the fuel storage (252) can be connected releasably to the heating unit.

14. The inhalation device according to claim 1,
wherein the outside wall disintegrates under the influence of heat or consists of a material or a material combination that becomes fragile under the influence of heat.

15. The inhalation device according to claim 1,
wherein the outside wall consists of heat-resistant wall segments that are joined by a joining means.

16. The inhalation device according to claim 1,
wherein the heating unit (350) is designed as a device that can be handled separately and that can be connected releasably to the inhalation mixture generator (370).

17. The inhalation device according to claim 1,
wherein an additive material storage that is designed separate from the inhalation mixture generator is provided, the additive material storage being designed so as to be replaceable or refillable.

18. A heating unit (50; 350) for use in an inhalation device (10; 110; 210; 310) for heating air and an additive material, comprising:
a combustion chamber (56; 156; 256) configured to form a flame to combust a fuel, the combustion chamber being in a flow-connection with the mouth of a user; and
an outside wall around the combustion chamber, the outside wall comprising
  a) an ignition access (226) through which the flame in the combustion chamber can be ignited and
  b) a plurality of micro openings (24; 124; 224) for supplying oxygen to the flame and for protecting the flame from wind gusts,
wherein the fuel inside the combustion chamber is ignited by pulling an external flame from a match or lighter through the ignition access when the user inhales, wherein the micro openings at least partially overlap the flame.

19. An inhalation device (210) for the inhalation administration of an inhalation mixture of air and at least one additive material comprising:
a substantially cylindrical outside wall (220);
a fuel storage (252) disposed at a distal end of the inhalation device (210);
a mouthpiece (282) disposed at a proximal end of the inhalation device (210);
a combustion chamber (256) disposed adjacent to and having an opening towards the fuel storage (252); and
an inhalation mixture generator (270) disposed adjacent to the combustion chamber (256) towards the proximal end of the inhalation device (210),
wherein the fuel storage (252), the combustion chamber (256), the inhalation mixture generator (270) and the mouthpiece (282) are arranged within the substantially cylindrical outside wall (220), and
wherein a combustion chamber wall section (222) of the substantially cylindrical outside wall (220) around the combustion chamber (256) comprises
  an ignition access (226) through which a flame in the combustion chamber can be ignited and
  micro openings (224) through which oxygen is provided to the flame within the combustion chamber, the micro openings being sufficiently small to protect the flame against gusts of wind, wherein the micro openings at least partially overlap the flame.

20. The inhalation device as in claim 19, wherein the ignition access comprises a plurality of elongated apertures.

21. The inhalation device as in claim 19, further comprising a fuel (258) with gel-like consistency within the fuel storage (252).

22. The inhalation device as in claim 19, wherein the fuel storage is made of chromium-nickel spring steel.

23. The inhalation device as in claim 21, wherein the fuel (258) within the fuel storage (252) is enclosed within a membrane (260) having low elasticity, and wherein the membrane (260) is torn open by compressing the fuel storage (252) before use.

* * * * *